US010295434B2

(12) United States Patent
Underwood et al.

(10) Patent No.: US 10,295,434 B2
(45) Date of Patent: May 21, 2019

(54) DIRECT FIELD ACOUSTIC TESTING SYSTEM, CONTROLS, AND METHOD

(75) Inventors: Marcos A. Underwood, Cupertino, CA (US); Robert Turk Goldstein, Crownsville, MD (US); Paul Alan Larkin, Mt. Airy, MD (US)

(73) Assignee: Marcos Underwood, Cupertino, CA (US)

( * ) Notice: Subject to any disclaimer, the term of this patent is extended or adjusted under 35 U.S.C. 154(b) by 222 days.

(21) Appl. No.: 13/117,940

(22) Filed: May 27, 2011

(65) Prior Publication Data

US 2012/0300580 A1 Nov. 29, 2012

(51) Int. Cl.
G01M 7/00 (2006.01)
G01N 29/04 (2006.01)

(52) U.S. Cl.
CPC ............. *G01M 7/00* (2013.01); *G01N 29/04* (2013.01)

(58) Field of Classification Search
CPC ................................ G01M 7/00; G01N 29/04
USPC .................................................... 73/584, 662
See application file for complete search history.

(56) References Cited

U.S. PATENT DOCUMENTS

| 4,989,158 A | 1/1991 | Sloane |
| 5,138,884 A | 8/1992 | Bonavia |
| 5,299,459 A | 4/1994 | Underwood |
| 5,638,004 A | 6/1997 | Combs et al. |
| 6,668,650 B1 | 12/2003 | Lafleur et al. |
| 2001/0032510 A1 | 10/2001 | Eagan et al. |
| 2003/0108208 A1 | 6/2003 | Thomas et al. |
| 2004/0024750 A1 | 2/2004 | Ulyanov et al. |

OTHER PUBLICATIONS

Underwood et. al.,"Filling in the MIMO Matrix, Part 1—Performing Random Tests Using Field Data", Sound and Vibration, Mar. 2011, pp. 8-14.*
"How to Divide Matrices," wikiHow [online], [retrieved on Sep. 25, 2017]. Retrieved from the Internet <URL:http://www.wikihow.com/Divide-Matrices>.*
Larkin et al., "Recent Developments in Direct Field Acoustic Testing", http://ntrs.nasa.gov/archive/nasa/casi.ntrs.nasa.gov/20120007347_2012007750.pdf, Oct. 2010.
International Search Report and Written Opinion, International Application No. PCT/US2012/039787, dated Aug. 24, 2012.

* cited by examiner

*Primary Examiner* — John E Chapman, Jr.
(74) *Attorney, Agent, or Firm* — Medler Ferro Woodhouse & Mills PLLC

(57) ABSTRACT

A direct field acoustic testing system includes at least one control microphone, a controller operatively coupled to the control microphone such that the controller receives at least one input signal from the control microphone, and at least four acoustic transducer groups operatively coupled to the controller such that each transducer is separately controllable by the controller such that a separate output signal is received by each transducer from the controller. A setup signal is applied to each of the acoustical transducers. The acoustic output of each of the acoustical transducers is monitored using the at least one control microphone. Assumptions regarding the relationship between the acoustic fields measured by the control microphones are made to enable the controller to reduce the number of calculations needed to compute error functions and corrected drive signals to be applied to the acoustic transducer groups.

20 Claims, 6 Drawing Sheets

DIRECT FIELD ACOUSTIC TESTING SYSTEM, CONTROLS, AND METHOD

BACKGROUND OF THE INVENTION

Field of the Invention

The present invention relates generally to the field of vibration testing of objects such as satellites, instrumentation or any other object whose reliability in operation may be evaluated using high intensity vibration testing. Specifically, the present invention relates to the use of direct field acoustic systems to perform vibration testing and to control means to increase the control bandwidth of direct field acoustic test systems having multiple outputs connected to separately driven groups of acoustical transducers.

Background of the Invention

The disclosure of co-pending U.S. application Ser. No. 13/117,870 filed May 27, 2011 is incorporated by reference herein in its entirety.

As disclosed in co-pending U.S. application Ser. No. 13/117,870 filed May 27, 2011 direct field acoustic test (DFAT) systems employing multiple separately controllable outputs driving separate groups of acoustic transducers have many advantages over prior art methods of performing acoustical vibration testing. However, the use of multiple separately controllable outputs connected to groups of separately driven acoustical transducers combined with the use of multiple microphones to provide separate control inputs leads to a geometric increase in the number and complexity of calculations required for real time control while a test is being performed. This in combination with the limitations of currently available hardware has placed certain limitations on the real time performance of multiple-input-multiple-output (MIMO) DFAT systems including limitations on the minimum frequency interval used for narrow band real time control, limitations on the maximum frequency for real time control to typically less than 2 kHz, limitations on the number of acoustical control inputs and separately controllable outputs as well as other limitations. In the performance of many types of acoustical vibration testing it is desirable to, for example, provide accurate control of the acoustic field at higher frequencies or use a larger number of control inputs and separately controlled outputs. Therefore it is desirable to provide a method of achieving faster real-time control of a MIMO DFAT system during closed loop operation.

SUMMARY OF THE INVENTION

Accordingly, in a MIMO DFAT system which employs multiple groups of separately controllable acoustical transducers, embodiments hereof provide a method and system which will increase the speed of the control means to permit more accurate real-time control of the acoustic field. More specifically, embodiments hereof increase the speed of the control means of a MIMO DFAT system which employs multiple groups of separately driven acoustical transducers by implementing certain experimentally determined assumptions regarding the relationship between the acoustic fields measured by the control microphones.

Embodiments hereof include a MIMO DFAT system preferably with at least four groups of acoustical transducers driven by four separately controllable drive signals and disposed in appropriate locations so as to provide an acoustic field having a high degree of spatial uniformity and low spatial coherence. Preferably at least four microphones are employed to measure the acoustic field at four separate locations and to provide preferably at least four control input signals. A controller or other processor is provided so as to provide real time control of the acoustic fields at the control locations. In mechanical vibration testing the relationship between the response at the control points is determined by the mechanical characteristics of the UUT and will be different for every test setup. However, in direct field acoustic testing it is desirable to produce an acoustic field which has minimal spatial variation and minimal coherence in order to simulate the characteristics of a reverberant field. Accordingly, the desired relationship between the acoustic fields at the control locations is the same regardless of the UUT and the test setup. Therefore, simplified reference spectrum data may be entered. These simplifications enable the control means to provide faster real time updates to the drive signals thereby extending the range of controlled frequencies to substantially above 2 kHz for the purpose of producing an acoustic field with pre-specified characteristics.

Embodiments hereof also include a MIMO DFAT system with a controller or other processor to provide real time control of the acoustic fields at the control locations. Simplified reference spectrum data is entered based on the relationship of the desired acoustic fields at the control locations. While performing a test only the magnitude component of the drive signals is updated in real time thereby enabling the control means to provide faster real time updates to the drive signals thereby extending the range of controlled frequencies to substantially above 2 kHz for the purpose of producing an acoustic field with pre-specified characteristics.

Embodiments hereof also include a MIMO DFAT system with equal numbers of separate control inputs and separately controllable outputs. This simplification enables the control means to provide faster real time updates to the drive signals thereby extending the range of controlled frequencies to substantially above 2 kHz for the purpose of producing an acoustic field with pre-specified characteristics.

Embodiments hereof also include a MIMO DFAT system with a controller or other processor to provide real time control of the acoustic fields at the control locations. Simplified reference spectrum data is entered except that different reference magnitude data is entered for one or more of the control locations. This simplification enables the control means to provide faster real time updates to the drive signals thereby extending the range of controlled frequencies to substantially above 2 kHz for the purpose of producing an acoustic field with pre-specified characteristics.

BRIEF DESCRIPTION OF THE DRAWINGS

Embodiments of the invention will now be described, by way of example only, with reference to the accompanying schematic drawings in which corresponding reference symbols indicate corresponding parts.

DETAILED DESCRIPTION OF EMBODIMENTS OF THE INVENTION

Figure 1:
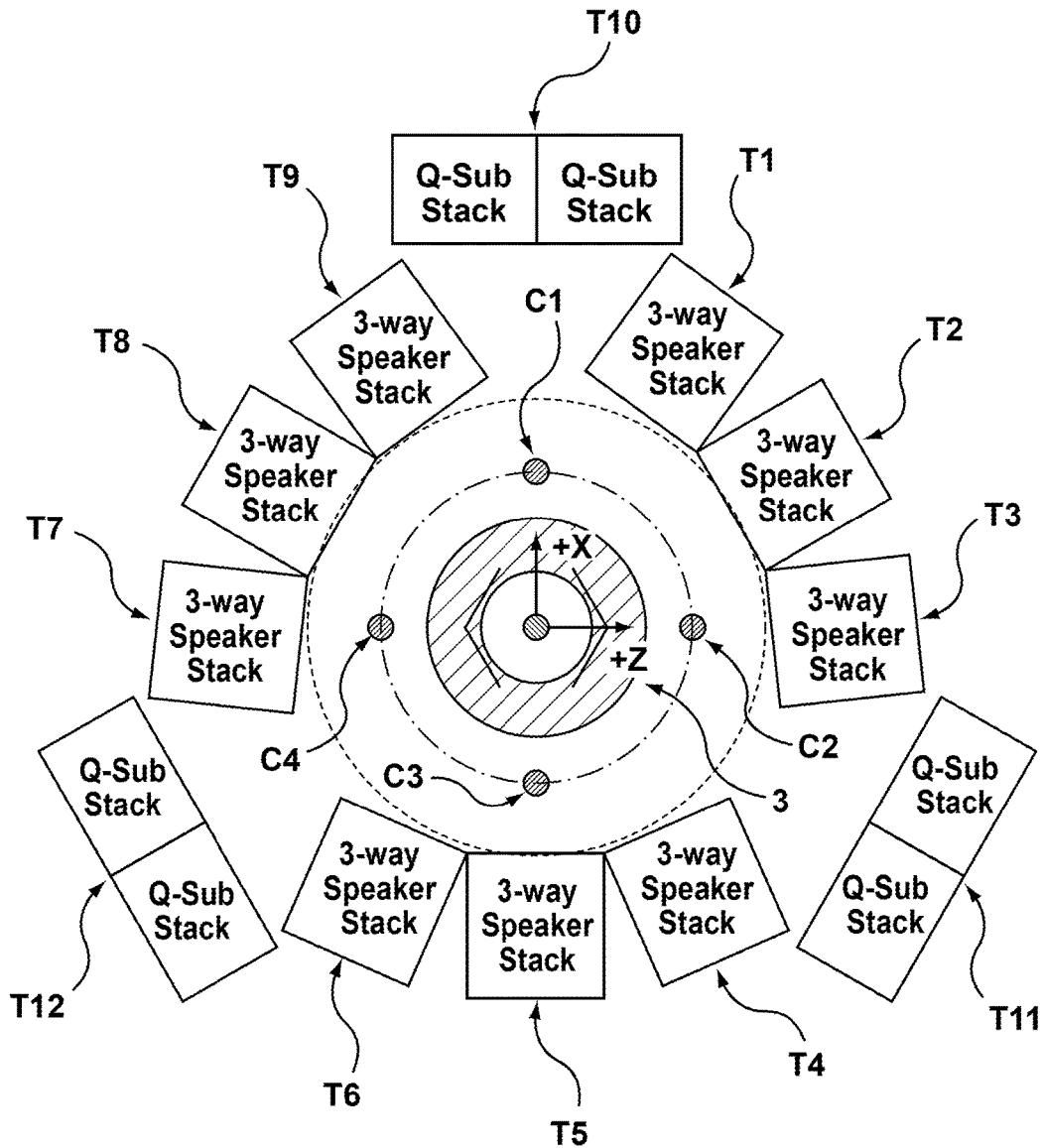
FIG. 1 is a schematic layout of an acoustic transducer group for direct field acoustic testing according to an embodiment hereof.

Embodiments hereof are now described with reference to the figures where like reference characters/numbers indicate identical or functionally similar elements. While specific configurations and arrangements are discussed, it should be understood that this is done for illustrative purposes only. A person skilled in the relevant art will recognize that other configurations and arrangements can be used without departing from the spirit and scope of the invention.

Referring to FIG. 1, an embodiment of a DFAT system includes a transducer array composed of electro-dynamic acoustic transducers T1-T9 covering various frequency ranges arrayed around the unit under test (UUT) 3 in a generally circular arrangement as shown. The transducer array is composed of three groups three-way speakers T1-T3, T4-T6, T7-T9 generally covering the frequency range above 100 Hz and three groups of electro-dynamic subwoofer loudspeakers T10-T12 generally covering the frequency range from 20 Hz to 200 Hz. Control microphones C1-C4 are disposed at various positions around the UUT 3 for the purpose of providing information about the acoustic field to the control system. In this embodiment each of the three groups of three-way speakers T1-T3, T4-T6, T7-T9 are driven by one of three separately controllable drive signals while the three groups of sub-woofers T10-T12 are driven together by a fourth separately controllable drive signal. Each of the four control microphones C1-C4 provides a separate control input. Therefore in this embodiment there are four control inputs and four separately controlled outputs.

Figure 2:
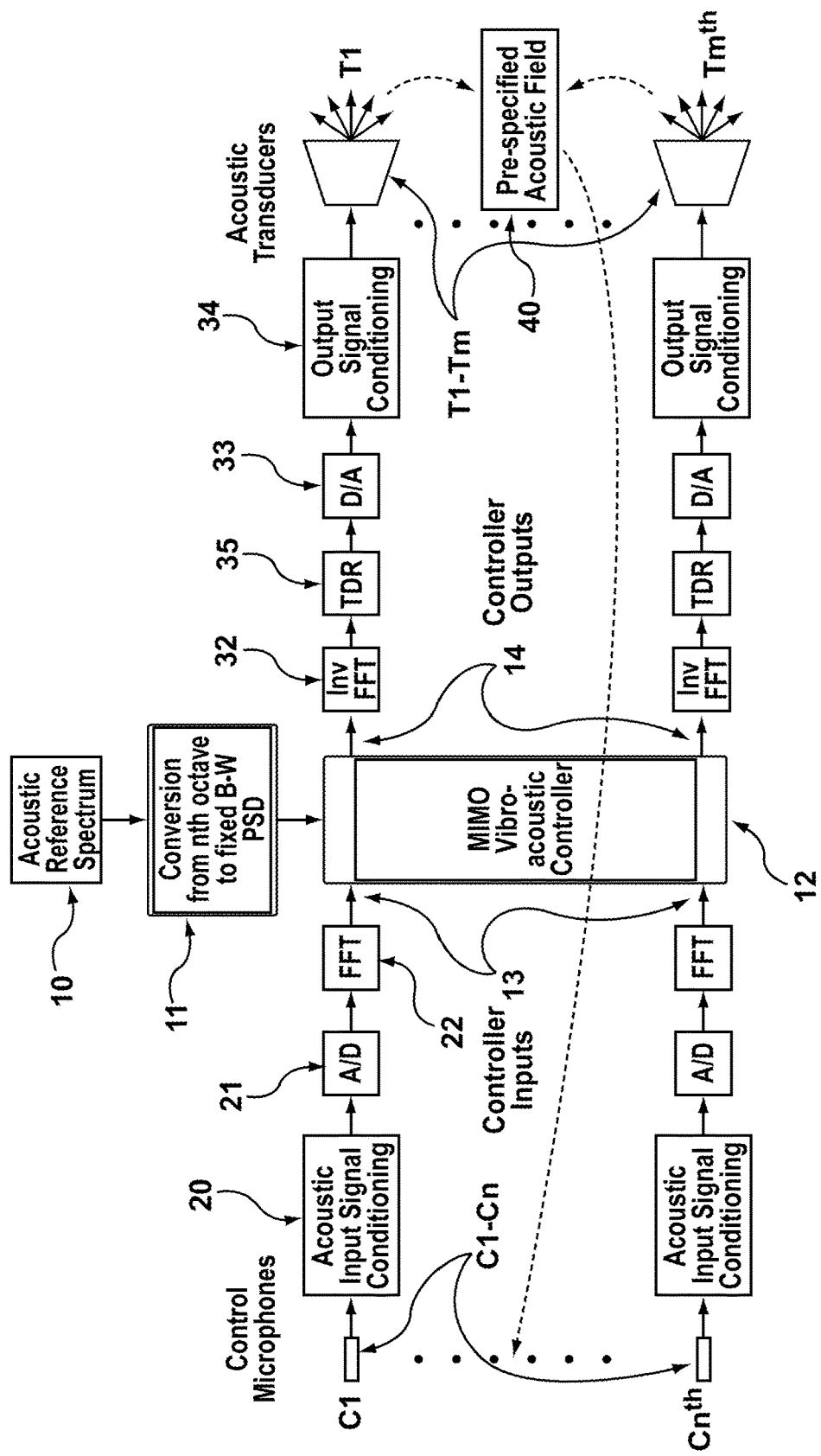
FIG. 2 is a simplified block diagram of a direct field acoustic testing system according to an embodiment hereof.

Referring to FIG. 2, a simplified block diagram of an embodiment hereof is shown. This is identical to FIG. 2 of co-pending U.S. application Ser. No. 13/117,870 filed May 27, 2011, which is incorporated by reference herein in its entirety. In this embodiment there are n=4 control microphones C1-C4 providing four separate controller inputs 13 and m=4 groups of acoustical transducers T1-T3, T4-T6, T7-T9, T10-T12 which are driven by four separately controllable controller outputs 14. Each of the control microphones C1-Cn produces electrical signals which are representative of the acoustic field at each microphone. Each of the electrical signals is conditioned in an input signal conditioner 20 according to the input requirements of a vibro-acoustic controller 12. By way of example and not of limitation, conditioner 20 may include anti-aliasing or other filters, application of microphone calibration data referenced to appropriate standards, and scaling of the signal to represent the proper units. An analog to digital converter 21 converts the conditioned electrical signals to a digital format and the digitized signals are converted to fixed band-width narrow-band power spectral densities by application of a Fast Fourier Transform (FFT), as represented in block 22 of FIG. 2. Each of these resulting data streams is connected to one input 13 of the vibro-acoustic controller 12. Those of ordinary skill in the art recognize that the input signal conditioner 20, A/D converter 21, and the FFT 22 may be part of the controller 12. Each output 14 from the controller 12 is converted from a narrow-band power spectral density to a digitized time series by an inverse FFT, as represented in block 32. This digitized time series may then be time domain randomized 35 depending on the type of test being conducted and then converted to an analog signal in digital to analog converter 33. Each analog signal is then conditioned in output signal conditioner 34 according to the input requirements of the amplification and acoustic transducers T1-Tm. By way of example and not of limitation, the conditioning may include additional filtering, gain, attenuation or power amplification. Each of the conditioned signals is then applied to the respective acoustical transducer group, T1-Tm. A pre-specified acoustical reference spectrum 10 is converted from the standard 1/nth octave format to a fixed band-width narrow-band power spectral density format which is consistent with the format of the signals from the control microphones C1-Cn and applied to the vibro-acoustic controller inputs 13. Those of ordinary skill in the art recognize that the inverse FFT 32, time domain randomization, the digital to analog converted 33, and the output signal conditioner may part of the controller 12.

Figure 3:
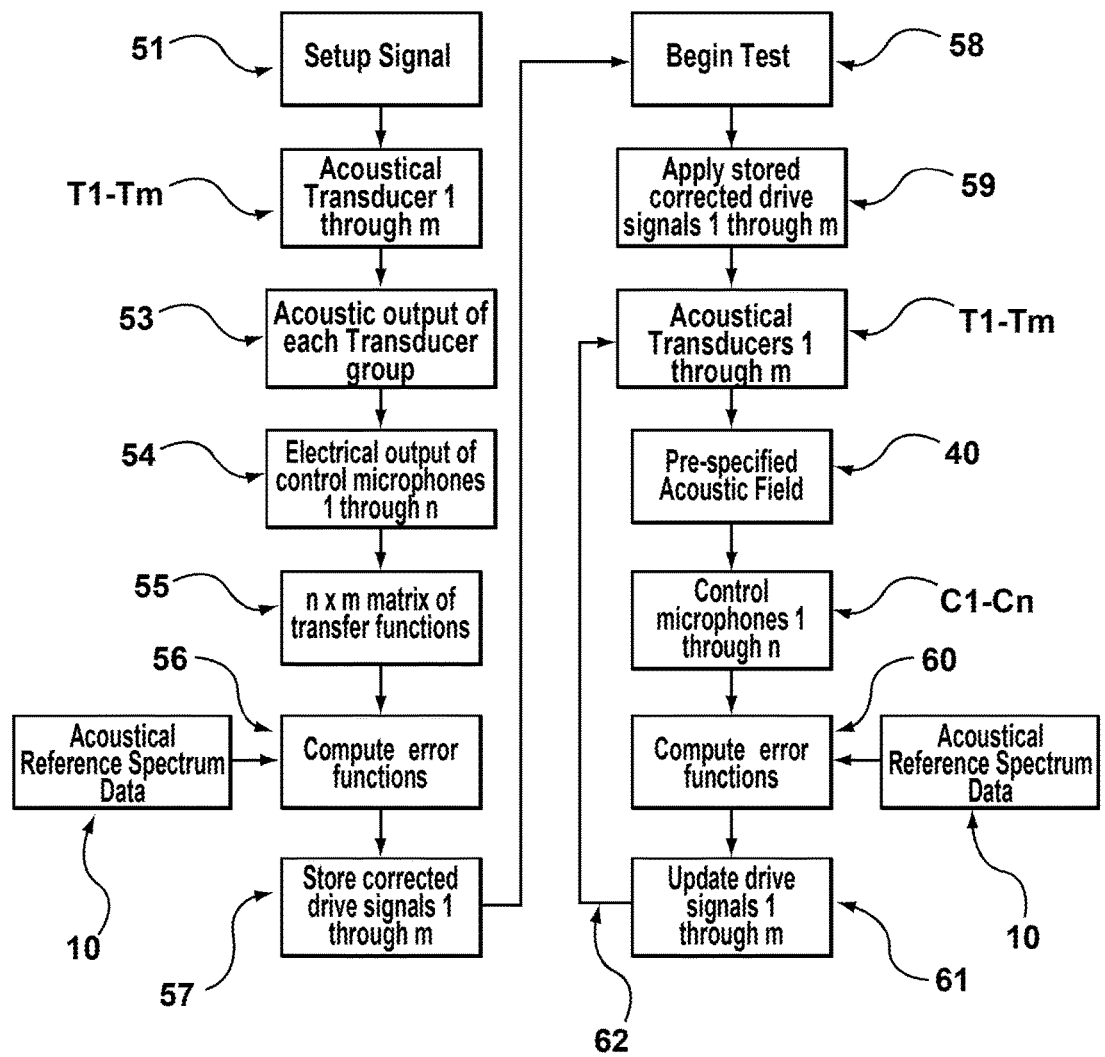
FIG. 3 is a simplified control diagram of an embodiment of the vibro-acoustic controller of the system of FIG. 2.

Referring now to FIG. 3, there is shown is a simplified block diagram which describes generally the functioning of an embodiment of a multiple-input-multiple-output (MIMO) vibro-acoustic controller 12. During the system identification process a signal 51 is applied to each of the acoustical transducer groups T1-Tm. The acoustic output 53 of each transducer group T1-Tm is separately monitored by each control microphone C1-Cn. The electrical output 54 of control microphones C1-Cn in response to each combination of transducer group and control microphone represent the transfer functions of each such combination and are recorded in an n×m matrix 55 where each element is one such transfer function. These transfer functions 55 are compared to the acoustical reference spectrum data 10. A matrix of error functions 56 is computed which is used to compute a corrected drive signal 57 for each of the transducer groups T1-Tm. In mechanical vibration testing and as will be familiar to those skilled in the art these may be expressed as:

$$\{C(f)\}=[H(f)]\{D(f)\}$$

Where $\{C(f)\}$ is the vector representing the acoustical reference spectrum data for each control location, $[H(f)]$ is the matrix of transfer functions between each control location 1 through n and the output of each group of acoustical transducers T1-Tm. $\{D(f)\}$ is the vector representing the corrected drive signals required to achieve the desired acoustical reference spectra $\{C(f)\}$.

At the start of the actual test 58 the previously stored 1 through m corrected drive signals 57 are applied 59 to the respective transducer groups T1-Tm. The resulting acoustic field is monitored by the control microphones C1-Cn and their outputs are compared to the acoustical reference spectrum data 10 from which error functions 60 are computed. These error functions 60 are used to update the drive signals 61 which are applied through control loop 62 to the respective transducer groups. In this embodiment, preferably there are at least n=4 control microphones and m=4 separately controllable transducer groups. However, embodiments with up to 16 microphones and 16 separately controllable transducer groups are possible.

As will be familiar to those skilled in the art the reference spectrum data for mechanical MIMO vibration testing is a matrix known as the spectral density matrix (SDM) which is often expressed as $[G_{RR}(f)]$. The diagonal terms of the SDM, $g_{nn}(f)$, contain the reference power spectral density (PSD) for each of the control inputs whereas the off diagonal terms of the SDM, $g_{nm}(f)$, contain the reference cross spectral density (CSD) expressing the relationship between each combination of control inputs. In addition to magnitude data the elements of the SDM contain reference phase and coherence data. It has been demonstrated that for mechanical vibration testing (see "Filling in the MIMO Matrix", Underwood et. al., Sound and Vibration, March 2011) accurately measured reference CSD data, including phase and coherence relationships, is required for mechanical MIMO vibration testing. However, when taking into account magnitude, phase and coherence relationships between the control locations, the calculations required to compute error functions and corrected drive signals are quite complex and the processing time required during real-time closed loop operation grows geometrically as the number of separate control inputs and separately controlled outputs increases. As a result MIMO testing whether mechanical or acoustical has been heretofore limited to closed loop real-time control of frequencies below approximately 2 kHz.

Direct field acoustic testing is fundamentally different from mechanical vibration testing in several crucial respects. In mechanical testing the control locations are mechanically linked to each other and the relationships between them, CSD's, are uniquely determined by the mechanical characteristics of the UUT. To create the reference SDM for mechanical testing these CSD's must be accurately measured. Otherwise the test system may try to force the UUT to behave in a manner inconsistent with its mechanical structure thereby damaging the UUT. In direct field acoustical testing there is no mechanical connection between control locations. Since it is desirable to have low spatial magnitude variation between control locations with minimum phase correlation and low coherence between control locations the relationship between the acoustical fields at the control locations is the same regardless of the test setup or the nature of the device being tested. Therefore, in MIMO direct field acoustic testing it is not necessary to measure or specify the reference CSD's between control locations. In addition, since the desired acoustic field at each control location has the same characteristics only one reference PSD entry on the diagonal of the SDM is necessary to completely describe the desired acoustic field. As will be explained more fully below these simplifications can significantly increase the speed at which the separately controllable drive signals applied to the separate transducer groups can be updated.

Referring again to FIG. 2, in this embodiment, there preferably are n=4 control microphones C1-C4 providing four separate controller inputs 13 and m=4 groups of acoustical transducers T1-T3, T4-T6, T7-19, T10-T12 which are driven by four separately controllable controller outputs 14. Referring to FIG. 3 the system identification matrix or FRM, 55 would be expressed as:

$$[H(f)] = \begin{bmatrix} h_{11}(f) h_{12}(f) h_{13}(f) h_{14}(f) \\ h_{21}(f) h_{22}(f) h_{23}(f) h_{24}(f) \\ h_{31}(f) h_{32}(f) h_{33}(f) h_{34}(f) \\ h_{41}(f) h_{42}(f) h_{43}(f) h_{44}(f) \end{bmatrix}$$

Where each $h_{nm}(f)$ represents the transfer function between one control microphone and the output of one group of transducers. Each of these transfer functions is measured and recorded during the system identification process.

Accordingly the acoustical reference spectrum or SDM, 10 would be:

$$[G_{RR}(f)] = \begin{bmatrix} g_{11}(f) g_{12}(f) g_{13}(f) g_{14}(f) \\ g_{21}(f) g_{22}(f) g_{23}(f) g_{24}(f) \\ g_{31}(f) g_{32}(f) g_{33}(f) g_{34}(f) \\ g_{41}(f) g_{42}(f) g_{43}(f) g_{44}(f) \end{bmatrix}$$

where the diagonal terms of the $g_{nm}(f)$, contain the reference power spectral density (PSD) for each of the control inputs whereas the off diagonal terms of the, $g_{nm}(f)$, contain the reference cross spectral density (CSD) for each combination of control inputs.

According to an embodiment hereof the SDM may be simplified to:

$$[G_{RR}(f)] = \begin{bmatrix} g_{11}(f) & 0 & 0 & 0 \\ 0 & g_{11}(f) & 0 & 0 \\ 0 & 0 & g_{11}(f) & 0 \\ 0 & 0 & 0 & g_{11}(f) \end{bmatrix}$$

where $g_{11}(f)$ is the desired reference acoustic spectrum magnitude data for any one of the control locations. By setting the reference CSD's to zero, zero correlation and coherence between the control locations is implied. Use of the same reference magnitude data for each control location implies minimum spatial magnitude variation. As will be understood by those of ordinary skill in the art, many different mathematical techniques and algorithms may be used to calculate the corrections to the drive signals during operation. As will also be understood by those of ordinary skill in the art, the simplifications outlined above may be used in a MIMO DFAT system to reduce the number and complexity of calculations required thereby increasing the maximum speed of the controller means that is employed. Therefore a system in accordance with this embodiment may provide real-time control of a MIMO DFAT system over a frequency range extending substantially above 2 kHz. Additionally, in a MIMO DFAT system in accordance with this embodiment employing twelve (12) control microphones and twelve (12) separately controllable groups of transducers, real time control to frequencies above 10 kHz has been demonstrated.

In another embodiment hereof, in a MIMO DFAT system and referring to FIG. 3, the system identification process including computation and storage of corrected drive signals 57 is performed as previously described herein or in co-pending U.S. application Ser. No. 13/117,870 filed May 27, 2011. The reference acoustical spectrum data 10 is also entered as previously described. Thereafter, only the magnitude response of the drive signals is corrected during real time closed loop operation 62. Real time control of phase and coherence relationships between the acoustical fields at the control locations are therefore suppressed which further simplifies the number and complexity of calculations required to update the drive signals during operation thereby further increasing the speed of the controller means being used. In a MIMO DFAT system in accordance with this embodiment employing twelve (12) control microphones and twelve (12) separately controllable groups of transducers, real time control to frequencies above 10 kHz has been demonstrated.

In another embodiment hereof, in a MIMO DFAT system and referring to FIG. 2, the number of control microphones C1-Cn and separately controllable groups of transducers T1-Tm are equal. The use of only square matrices has been shown to further simplify the number and complexity of calculations required to update the drive signals during operation thereby further increasing the speed of the controller means being used. In a MIMO DFAT system in accordance with this embodiment employing twelve (12) control microphones and twelve (12) separately controllable groups of transducers, real time control to frequencies above 10 kHz has been demonstrated.

In another embodiment hereof, in a MIMO DFAT system and referring to FIG. 3, the reference acoustical spectrum data 10 is entered as previously described except that at least two of the reference acoustical spectra representing the desired acoustical field at two of the control microphones and represented by the diagonal elements of the SDM are different. In some cases it is desirable to accurately characterize specific variations in the acoustic field experienced by a device during operation or while being placed into service. In this embodiment different magnitude data for the reference acoustical spectra may be entered for one or more control locations. In combination with the simplifications of previously described embodiments it has been shown that it is possible to provide real time control at frequencies substantially above 2 kHz while controlling for reference acoustical spectra which are different at up to 12 control locations. In a MIMO DFAT system in accordance with this embodiment employing 12 control microphones and 12 separately controllable groups of transducers, real time control to frequencies above 10 kHz has been demonstrated.

Figure 4:
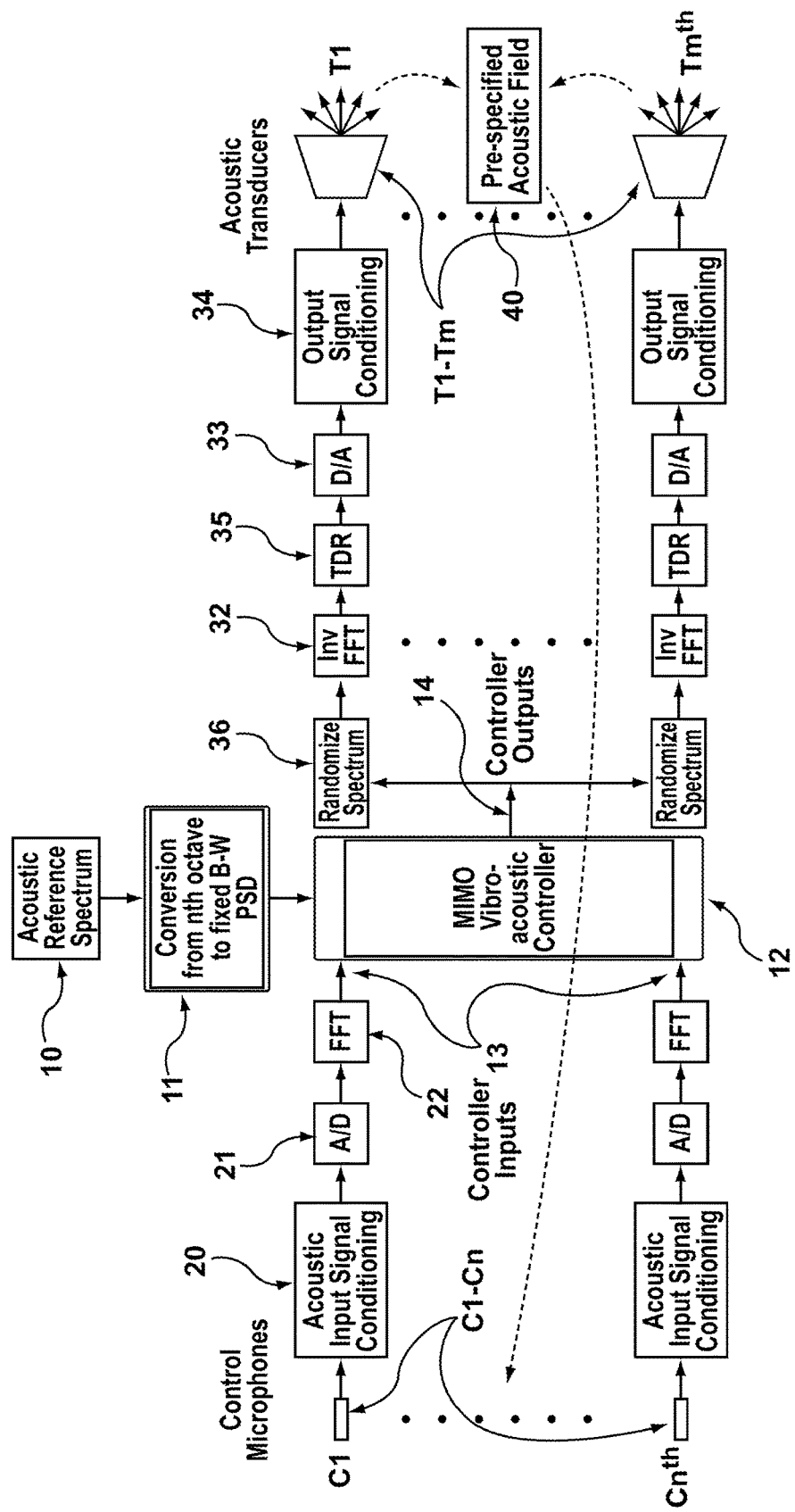
FIG. 4 is a simplified block diagram of a direct field acoustic testing system according to another embodiment hereof.

Referring to FIG. 4, a simplified block diagram of a modified multiple-input-single output (MISO) DFAT system in accordance with another embodiment is shown. For purposes of increasing the speed of the system to enable real time control over a broader bandwidth during closed loop operation, it may be desirable to use a single controllable output 14 from the controller 12. In accordance with this embodiment, the output signal 14 from controller 12 is split into m separate signal paths corresponding to separately driven acoustical transducers T1-Tm. The spectrum of each signal path is independently randomized 36 using white noise sequences prior to conversion to a digitized time series by inverse FFT 32. The remaining features shown in FIG. 4 are as described with respect to FIG. 2 and are marked with the same reference numerals. The coherence of the acoustic field produced at the control microphones by this method is not generally as low as methods employing multiple separately controllable outputs, but is substantially better than standard MISO techniques and may be an acceptable compromise where a high speed MIMO controller is not available.

Figure 5:
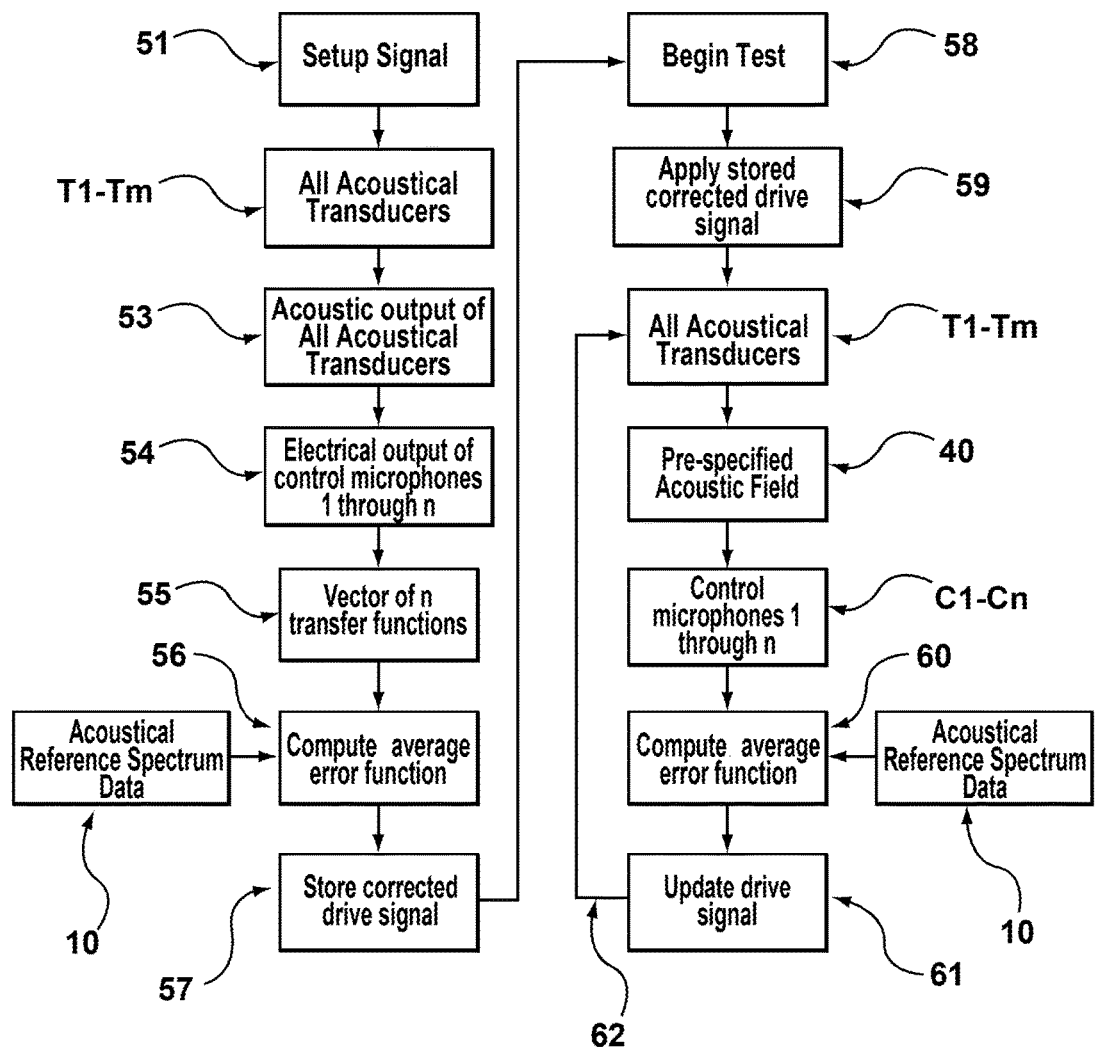
FIG. 5 is a simplified control diagram of an embodiment of the vibro-acoustic controller of the system of FIG. 4.

Referring to FIG. 5, during the system identification process a signal 51 is applied to all of the acoustical transducer groups T1-Tm. The combined acoustic output of the acoustical transducers 53 is separately monitored by each control microphone C1-Cn. The electrical output 54 of control microphones C1-Cn in response to the combined output of all of the transducers T1-Tm are recorded as a vector of n transfer functions 55. These transfer functions 55 are compared to the acoustical reference spectrum data 10 and an average error function 56 is computed for the purpose of computing a corrected drive signal 57. While a test is being performed the corrected drive signal 57 is applied 59 to the signal paths for all of the acoustical transducers T1-Tm. The acoustic field 40 is monitored by the control microphones C1-Cn and an average error function 60 is computed for the purpose of updating the drive signal 61 which is applied to the signal paths for all of the acoustical transducers via feedback loop 62.

Figure 6:
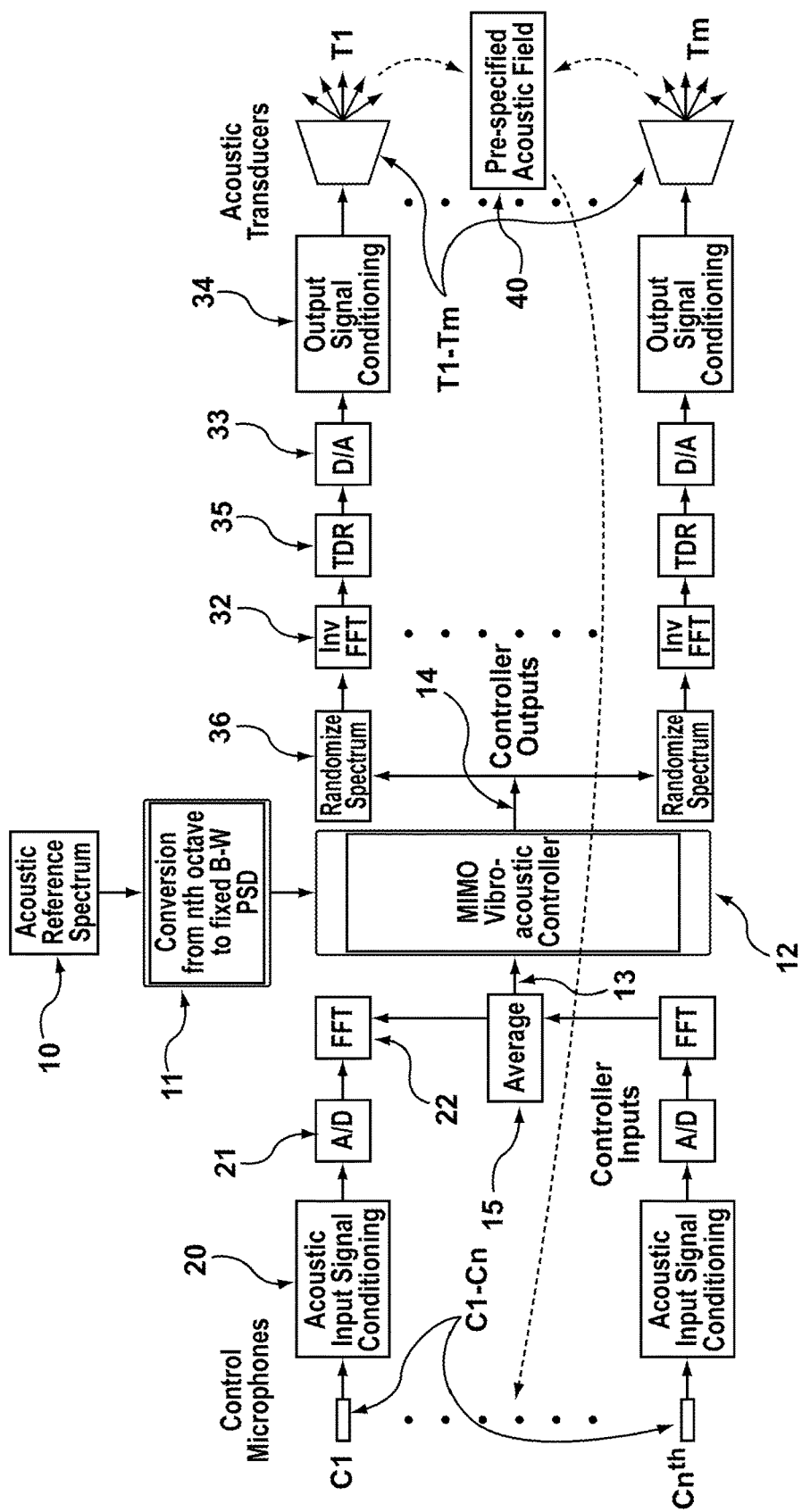
FIG. 6 is a simplified block diagram of a direct field acoustic testing system according to another embodiment hereof.

Referring to FIG. 6, an alternative implementation of this embodiment is shown in which the outputs of the control microphones C1-Cn are averaged 15 prior to being processed by the controller 12. The remaining features shown in FIG. 6 are as described with respect to FIG. 4 and are marked with the same reference numerals. In either variation of this embodiment, preferably the number of separately driven transducers T1-Tm is at least four and at least one control microphone C1 is used. However, up to sixteen separately driven transducers and sixteen or more control microphones may be used.

It will be apparent to those skilled in the art that many more variations may be implemented which fall within the scope of the present invention. These may include by way of example and not of limitation; differing types or numbers of transducers, differing numbers of inputs and outputs, different transducer array layouts, alternate configuration or connection of transducer sub-arrays to said outputs, choices of locations for control or monitoring, any suitable type of multiple-input-multiple-output control system or logic, different types of or combinations signals for use during operation, or any other circumstances in which the disclosed multiple output techniques are applied to a direct field acoustic testing system.

What is claimed is:

1. A method of direct field acoustic testing of a unit under test comprising the steps of:
   positioning at least four acoustic transducer groups and at least one control microphone around the unit under test;
   applying a setup signal to each of the acoustical transducers;
   separately monitoring the acoustic output of each of the acoustical transducer groups using the at least one control microphone to create a matrix of transfer functions representing an output signal of each control microphone with respect to each acoustical transducer group;
   computing corrected drive signals corresponding to the acoustical transducer groups by comparing the matrix of transfer functions to a reference spectrum, wherein the reference spectrum is expressed as a matrix containing only reference power spectral density functions for each control input corresponding to the acoustic field at the location of each control microphone such that reference cross spectral density functions for each combination of control inputs are set to zero; and
   applying each corrected drive signal to the respective acoustical transducer group.

2. The method of claim 1 wherein the reference spectrum is expressed as a fixed band-width narrow band spectral density.

3. The method of claim 2, wherein the band-width of the fixed band-width narrow band spectral density is less than or equal to 12.5 Hz.

4. The method of claim 1, further comprising the steps of:
   after applying the corrected drive signals to the acoustical transducer groups, monitoring the acoustic output of the acoustical transducer groups using the at least one control microphone;
   comparing an updated output of the at least one control microphone in response to the corrected drive signals with respect to all of the acoustical transducer groups to the reference spectrum to create an updated matrix of error functions;
   computing an updated corrected drive signal for each acoustical transducer group; and applying each updated corrected drive signal to the respective acoustical transducer group.

5. The method of claim 4 wherein the drive signals are updated in real time.

6. The method of claim 4 wherein the reference power spectral density functions for all of the control inputs are the same.

7. A method of direct field acoustic testing of a unit under test comprising the steps of:
positioning at least four acoustic transducer groups and a plurality of control microphones around the unit under test;
applying a setup signal to each of the acoustical transducers;
separately monitoring the acoustic output of each of the acoustical transducer groups using the control microphones to create a matrix of transfer functions representing an output signal of each control microphone with respect to each acoustical transducer group;
computing corrected drive signals corresponding to the acoustical transducer groups by comparing the matrix of transfer functions to a reference spectrum;
applying each corrected drive signal to the respective acoustical transducer group;
after applying the corrected drive signals to the acoustical transducer groups, monitoring the acoustic output of each of the acoustical transducer groups using the control microphones;
comparing only a magnitude response of an updated output of each control microphone in response to the corrected drive signals with respect to all of the acoustical transducer groups to the reference spectrum to create an updated matrix of error functions, wherein the control of phase and coherence relationships between acoustical fields at the control microphone locations is suppressed;
computing an updated corrected drive signal for each acoustical transducer group; and
applying each updated corrected drive signal to the respective acoustical transducer group.

8. The method of claim 7 wherein the reference spectrum is expressed as a fixed band-width narrow band spectral density.

9. The method of claim 8, wherein the band-width of the fixed band-width narrow band spectral density is less than or equal to 12.5 Hz.

10. The method of claim 7, wherein the drive signals are updated in real time.

11. A method of direct field acoustic testing of a unit under test comprising the steps of:
positioning at least four separately controllable acoustic transducer groups and at least four control microphones around the unit under test, wherein the number of separately controllable acoustic transducer groups and the number of separate control inputs from the control microphones is equal;
applying a setup signal to each of the acoustical transducers;
separately monitoring the acoustic output of each of the acoustical transducer groups using the control microphones to create a square matrix of transfer functions representing an output signal of each control microphone with respect to each acoustical transducer group;
computing corrected drive signals corresponding to the acoustical transducer groups by comparing the matrix of transfer functions to a reference spectrum; and applying each corrected drive signal to the respective acoustical transducer group.

12. The method of claim 11 wherein the reference spectrum is expressed as a fixed band-width narrow band spectral density.

13. The method of claim 12, wherein the band-width of the fixed band-width narrow band spectral density is less than or equal to 12.5 Hz.

14. The method of claim 11, further comprising the steps of:
after applying the corrected drive signals to the acoustical transducer groups, monitoring the acoustic output of the acoustical transducer groups using the control microphones;
comparing an updated output of each control microphone in response to the corrected drive signals with respect to all of the acoustical transducer groups to the reference spectrum to create an updated matrix of error functions;
computing an updated corrected drive signal for each acoustical transducer group; and
applying each updated corrected drive signal to the respective acoustical transducer group.

15. The method of claim 14, wherein the drive signals are updated in real time.

16. A method of direct field acoustic testing of a unit under test comprising the steps of:
positioning at least four acoustic transducer groups and a plurality of control microphones around the unit under test;
applying a setup signal to each of the acoustical transducers;
separately monitoring the acoustic output of all of the acoustical transducer groups using the plurality of control microphones to create a vector of transfer functions equal to the number of control microphones;
computing a corrected drive signal by comparing the matrix of transfer functions to a reference spectrum;
splitting the corrected drive signal into separate drive signals corresponding to the number of acoustic transducer groups;
independently randomizing the spectrum of each separate drive signal;
applying the independently randomized separate drive signal to the corresponding acoustical transducer group.

17. The method of claim 16 wherein the reference spectrum is expressed as a fixed band-width narrow band spectral density.

18. The method of claim 17, wherein the band-width of the fixed band-width narrow band spectral density is less than or equal to 12.5 Hz.

19. The method of claim 16, further comprising the steps of:
after applying the independently randomized separate drive signals to the acoustical transducer groups, monitoring the acoustic output of each of the acoustical transducer groups using the at least one control microphone;
comparing an updated output of the at least one control microphone with respect to all of the acoustical transducer groups to the reference spectrum to create an updated average error function;
computing an updated corrected drive signal for each acoustical transducer group; and
applying each updated corrected drive signal to the respective acoustical transducer group.

20. The method of claim 19, wherein the drive signals are updated in real time.

\* \* \* \* \*